United States Patent [19]
Bender et al.

[11] Patent Number: 5,948,777
[45] Date of Patent: Sep. 7, 1999

[54] CANNABINOID RECEPTOR AGONISTS

[75] Inventors: Paul Elliot Bender, Cherry Hill, N.J.; Siegfried Benjamin Christensen, IV, Philadelphia, Pa.

[73] Assignee: SmithKline Beecham Corporation, Philadelphia, Pa.

[21] Appl. No.: 09/051,828

[22] PCT Filed: Mar. 18, 1998

[86] PCT No.: PCT/US98/05352

§ 371 Date: May 1, 1998

§ 102(e) Date: May 1, 1998

[87] PCT Pub. No.: WO98/41519

PCT Pub. Date: Sep. 24, 1998

Related U.S. Application Data

[60] Provisional application No. 60/040,808, Mar. 18, 1997, and provisional application No. 60/043,060, Apr. 4, 1997.

[51] Int. Cl.$^6$ .............. A61K 31/415; A61K 31/535; C07D 231/20; C07D 413/12

[52] U.S. Cl. .............. 514/235.8; 514/407; 544/140; 546/211; 546/276.1; 548/369.7

[58] Field of Search .............. 544/140; 546/211, 546/276.1; 548/369.7; 514/235.8, 407

[56] References Cited

U.S. PATENT DOCUMENTS

| | | | |
|---|---|---|---|
| 5,217,523 | 6/1993 | Ditrich et al. | 548/374.1 |
| 5,556,987 | 9/1996 | Aoki et al. | 548/369.7 |
| 5,750,721 | 5/1998 | Gallenkamp et al. | 548/374.1 |

*Primary Examiner*—Robert W. Ramsuer
*Attorney, Agent, or Firm*—Soma G. Simon; William T. King; Charles M. Kinzig

[57] ABSTRACT

Novel pyrazole derivatives are provided which are cannabinoid receptor agonists.

12 Claims, No Drawings

CANNABINOID RECEPTOR AGONISTS

This application claims benefit from U.S. application 60/040,808 filed Mar. 18, 1997 and 60/043,060 filed Apr. 4, 1997.

FIELD OF THE INVENTION

The present invention relates to novel pyrazole derivatives, pharmaceutical compositions containing these compounds and their use as cannabinoid peripheral receptor agonists.

BACKGROUND OF THE INVENTION

Cannabinoids are a specific class of psychoactive compounds present in Indian cannabis (*Cannabis sativa*), including about sixty different molecules, the most representative being cannabinol, cannabidiol and several isomers of tetrahydrocannabinol. Knowledge of the therapeutic activity of cannabis dates back to the ancient dynasties of China, where, 5,000 years ago, cannabis was used for the treatment of asthma, migraine and some gynaecological disorders. These uses later became so established that, around 1850, cannabis extracts were included in the US Pharmacopaeia and remained there until 1947.

Cannabinoids are known to cause different effects on various systems and/or organs, the most important being on the central nervous system and on the cardiovascular system. These effects include alterations in memory and cognition, euphoria, and sedation. Cannabinoids also increase heart rate and vary systemic arterial pressure. Peripheral effects, such as bronchial dilation, immunomodulation, and downregulation of inflammation have also been observed. The capability of cannabinoids to reduce intraocular pressure and to affect respiratory and endocrine systems is also well documented. See e.g. L. E. Hollister, Health Aspects of Cannabis, *Pharmacological Reviews*, Vol. 38, pp. 1–20, (1986). More recently, it was found that cannabinoids suppress the cellular and humoral immune responses and exhibit antiinflammatory properties. Wirth et al., Antiinflammatory Properties of Cannabichrome, *Life Science*, Vol. 26, pp. 1991–1995, (1980).

In spite of the foregoing benefits, the therapeutic use of cannabis is controversial, due to its psychoactive effects. Although work in this field has been ongoing since the 1940's, evidence indicating that the peripheral effects of cannabinoids are directly mediated, and not secondary to a CNS effect, has been limited by the lack of receptor characterization, the lack of information concerning an endogenous cannabinoid ligand and, until recently, the lack of receptor subtype selective compounds.

The first cannabinoid receptor was found to be mainly localized in the brain, and, only to a lesser extent, in peripheral tissues. In view of its mRNA localization, it was designated the central receptor ("CB1"). See Matsuda et al., "Structure of a Cannabinoid Receptor and Functional Expression of the Cloned cDNA," *Nature*, Vol. 346, pp. 561–564 (1990. The second cannabinoid receptor ("CB2") was localized primarily to the spleen with low expression in the CNS, and was postulated to modulate the non psychoactive effects of the cannabinoids. See Munro et el., "Molecular Characterization of a Peripheral Receptor for Cannabinoids," *Nature*, Vol. 365, pp. 61–65 (1993).

The foregoing indications and the preferential localization of the CB2 receptor in the immune system suggest a specific role of CB2 in modulating the immune and antiinflammatory response of cannabinoids.

The role of CB2 in immunomodulation, inflammation, osteoporosis, cardiovascular, renal and other disease conditions is currently under examination. In light of the fact that cannabinoids act on receptors capable of modulating different functional effects, and in view of the low homology between CB2 and CB 1, the importance of developing a class of drugs selective for the CB2 receptor subtype is evident. The natural or synthetic cannabinoids currently available do not fulfill this function because they are active on both receptor subtypes.

Based on the foregoing, there is a need for compounds which are capable of selectively activating the peripheral cannabinoid receptor. Thus, CB2 agonists offer a unique approach toward the pharmacotherapy of immune disorders, inflammation, osteoporosis, renal ischemia and other pathophysiological conditions.

Recently, some compounds have been prepared and reported capable of acting as agonists on both cannabinoid receptors. For example, use of derivatives of dihydroxypyrrole-(1,2,3-d,e)-1,4-benzoxazine in the treatment of glaucoma and the use of derivatives of 1,5-diphenylpyrazole as immunomodultors or psychotropic agents in the treatment of various neuropathologies, migraine, epilepsy, glaucoma, etc are known. See U.S. Pat. No. 5,112,820 and EP 576357, respectively. However, because these compounds are active on both the CB1 and CB2 receptor, they can lead to serious psychoactive effects. Also recently described are indole derivatives which are reported to selectively bind to CB2 over CB1 receptors. See Michel Gallant et al, Bioorganic & Medicinal Chemistry Letters, 6(19), pp. 2263–2268 (1996).

SUMMARY OF THE INVENTION

The present invention provides novel pyrazole derivatives represented by Formula (I) and pharmaceutical compositions containing these compounds, and their use as CB2 receptor agonists which are useful in the treatment of a variety of diseases including but not limited to immune disorder, inflammation, osteoporosis, psoriasis, eczema and renal ischemia.

The present invention further comprises a method for activating CB2 receptors in an animal, including humans, which comprises administering to an animal in need thereof an effective amount of a compound of Formula (I).

DETAILED DESCRIPTION OF THE INVENTION

The compounds of the present invention are represented by structural Formula (I):

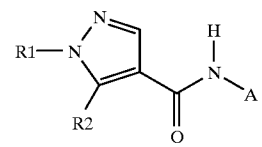

Formula (I)

wherein:

A is selected from the group consisting of 1-adamantyl, 2-adamantyl, 3-noradamantyl, and 1,1,3,3-tetramethylbutyl;

$R_2$ is selected from the group consisting of 2-(4-morpholino)ethoxy, 2-(diallylamino)ethoxy, 2-, 3-, or 4-pyridylmethoxy, 2-(diethylamino)ethoxy, 1-methylpiperidinyl-2-methoxy, benzyloxy and 4-substituted benzyloxy; where the substituent is selected from the group consisting of hydrogen, fluoro, chloro, methoxy, methylthio, and nitro; and $R_1$ is selected from the group consisting of $C_{1-6}$ alkyl, 3- or 4-biphenyl, unsubstituted or substituted by halo, 1-naphthyl, benzyl, phenethyl, phenyl, monosubstituted phenyl, wherein the substituent is selected from the group consisting of hydrogen, $C_{1-4}$ alkyl, fluoro, chloro, bromo, methoxy, trifluoromethyl, and nitro, or disubstituted phenyl where the substituents are, independently, selected from the group consisting of fluoro, chloro, or methyl.

Also included in the present invention are pharmaceutically-acceptable salt complexes. Preferred salt complexes include hydrochloride, hydrobromide, citrate, tartrate, malate, maleate, lactate, fructose 1,6-diphosphate, phosphate, succinate, sulfate, aspartate, adipate, methanesulfonate, lauryl sulfate, diguaiacyl phosphate, diacetyl sulfate, glutamate, gluconate, and edetate.

All alkyl and alkoxy groups may be straight or branched. The compounds of the present invention may contain one or more asymmetric carbon atoms and may exist in racemic and optically active forms. All of these compounds and diastereomers are contemplated to be within the scope of the present invention.

As used herein, "allyl" means $-CH_2=CH-CH_2-$.

In preferred compounds of the present invention, A is 1-adamantyl, 2-adamantyl, or 3-noradamantyl; $R_2$ is selected from the group consisting of 2-(4-morpholino)ethoxy, 4-pyridylmethoxy, 1-methylpiperidinyl-2-methoxy, benzyloxy, and 4-fluoro-benzyloxy, and $R_1$ is phenyl, benzyl, or 4-monosubstituted phenyl wherein the substitutent is selected from the group consisting of $C_{1-4}$ alkyl, fluoro, chloro, methoxy, and trifluoromethyl.

In more preferred compounds of the present invention, A is 1-adamantyl; $R_2$ is selected from the group consisting of 2-(4-morpholino)ethoxy, 4-pyridylmethoxy, and 1-methylpiperidinyl-2-methoxy; and $R_1$ is phenyl, benzyl, or 4-monosubstituted phenyl wherein the substitutent is selected from the group consisting of $C_{1-4}$ alkyl, fluoro, chloro, and methoxy.

In even more preferred compounds of the present invention, $R_2$ is 2-(4-morpholino)ethoxy, and $R_1$ is phenyl; or 4-monosubstituted phenyl wherein the substituent is $C_{1-4}$ alkyl.

Preferred compounds useful in the present invention are selected from the group consisting of:

N-(1-Adamantyl)-1-(4-isopropylphenyl)-5-(2-(4-morpholino)ethoxy)pyrazole-4-carboxamide, N-(1-Adamantyl)-1-(4-(2,6-dichlorophenyl)phenyl)-5-(2-(4-morpholino)ethoxy)pyrazole-4-carboxamide, N-(2-Adamantyl)-1-(4-fluorophenyl)-5-(4-pyridylmethoxy)pyrazole-4-carboxamide, N-(3-Noradamantyl)-1-(4-chlorophenyl)-5-(1-methylpiperidinyl-2-methoxy)pyrazole-4-carboxamide, N-(1,1,3,3-Tetramethylbutyl)-5-(4-fluorobenzyloxy)-1-(4-methoxyphenyl)pyrazole-4-carboxamide, N-(1-Adamantyl)-1-(2,5-difluorophenyl)-5-(2-(4-morpholino)ethoxy)pyrazole-4-carboxamide, N-(1-Adamantyl)-1-(2,3-dimethylphenyl)-5-(2-(4-morpholino)ethoxy)pyrazole-4-carboxamide, N-(1-Adamantyl)-5-(2-(4-morpholino)ethoxy)-1-(phenethyl)pyrazole-4-carboxamide, N-(1-Adamantyl)-1-benzyl-5-(2-(4-morpholino)ethoxy)pyrazole-4-carboxamide, N-(1-Adamantyl)-1-benzyl-5-(2-diallylaminoethoxy)pyrazole-4-carboxamide, N-(2-Adamantyl)-1-(4-bromophenyl)-5-(4-methylthiobenzyloxy)pyrazole-4-carboxamide, N-(3-Noradamantyl)-5-(benzyloxy)-1-(4-chlorophenyl)pyrazole-4-carboxamide, N-(1,1,3,3-Tetramethylbutyl)-5-(4-chlorobenzyloxy)-1-(1-naphthyl)pyrazole-4-carboxamide, N-(1-Adamantyl)-1-(4-biphenyl)-5-(2-pyridylmethoxy)pyrazole-4-carboxamide, N-(2-Adamantyl)-5-(4-methoxybenzyloxy)-1-(4-trifluorophenyl)pyrazole-4-carboxamide, N-(3-Noradamantyl)-1-(4-nitrophenyl)-5-(3-pyridylmethoxy)pyrazole-4-carboxamide, N-(1,1,3,3-Tetramethylbutyl)-1-(1-hexyl)-5-(2-(4-morpholino)ethoxy)pyrazole-4-carboxamide, N-(1-Adamantyl)-1-(4-fluorophenyl)-5-(4-pyridylmethoxy)pyrazole-4-carboxamide, N-(2-Adamantyl)-5-(4-fluorobenzyloxy)-1-(4-methoxyphenyl)pyrazole-4-carboxamide, N-(1-Adamantyl)-1-(4-chlorophenyl)-5-(1-methylpiperidinyl-2-methoxy)pyrazole-4-carboxamide; and N-(1-Adamantyl)-1-phenyl-5-(4-pyridylmethoxy)pyrazole-4-carboxamide.

More preferred compounds useful in the present invention are selected from the group consisting of:

N-(1-Adamantyl)-1-(4-isopropylphenyl)-5-(2-(4-morpholino)ethoxy)pyrazole-4-carboxamide, N-(2-Adamantyl)-1-(4-fluorophenyl)-5-(4-pyridylmethoxy)pyrazole-4-carboxamide, N-(3-Noradamantyl)-1-(4-chlorophenyl)-5-(1-methylpiperidinyl-2-methoxy)pyrazole-4-carboxamide, N-(1-Adamantyl)-1-benzyl-5-(2-(4-morpholino)ethoxy)pyrazole-4-carboxamide, N-(2-Adamantyl)-5-(4-fluorobenzyloxy)-1-(4-methoxyphenyl)pyrazole-4-carboxamide, N-(3-Noradamantyl)-5-(benzyloxy)-1-(4-chlorophenyl)pyrazole-4-carboxamide, N-(1-Adamantyl)-1-(4-fluorophenyl)-5-(4-pyridylmethoxy)pyrazole-4-carboxamide, N-(1-Adamantyl)-1-(4-chlorophenyl)-5-(1-methylpiperidinyl-2-methoxy)pyrazole-4-carboxamide, and N-(1-Adamantyl)-1-phenyl-5-(4-pyridylmethoxy)pyrazole-4-carboxamide.

The most preferred compound useful in the present invention is:

N-(1-Adamantyl )-1-(4-isopropylphenyl)-5-(2-(4-morpholino)ethoxy)pyrazole-4-carboxamide.

The present invention provides compounds of Formula (I):

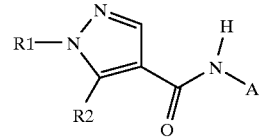

Formula (I)

which can be prepared by processes described in Schemes 1 and 2 below.

Scheme 1

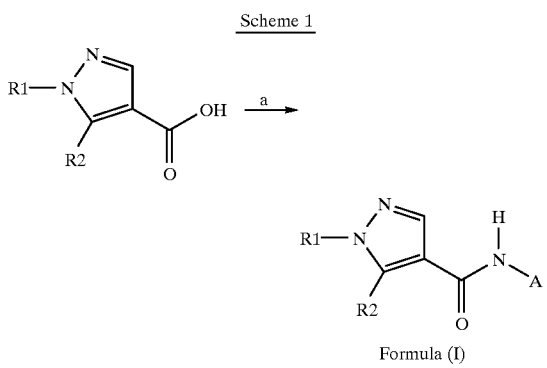

Formula (I)

a) HOBT, EDC, TEA, DMF, A-NH$_2$.

In Scheme 1, above, the pyrazole-5-carboxylic acids are converted to the N-alkyl pyrazole-5-carboxamides by standard amide coupling chemistry (by reacting with 1-hydroxybenzotriazine hydrate ("HOBT"), 1-(3-dimethylaminopropyl)-3-ethylcarbodiimide ("EDC"), triethylamine ("TEA"), and 1-adamantane amine hydrochloride, in dimethylfornamide ("DMF")).

Scheme 2

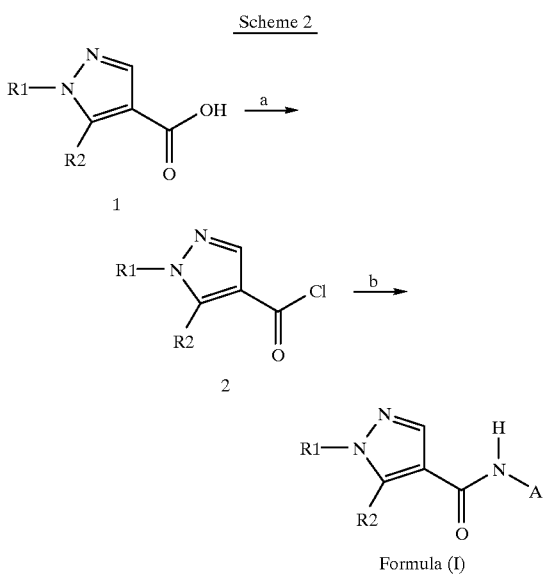

Formula (I)

a) thionyl chloride, b) methylene chloride, A-amine, NaHCO$_3$

An alternative and preferred process, shown in Scheme 2, above, consists of:

a) converting the pyrazole-5-carboxylic acid 1 to the pyrazole-5-carbonyl chloride 2 employing standard conditions (such as treating with thionyl chloride either neat or in the presence of an inert solvent, or with oxalyl chloride in a suitable solvent such as benzene in presence of a catalytic amount of N,N-dimethylformamide) followed by:

b) treating the acid chloride 2 in an inert solvent (e.g. chloroform, methylene chloride, toluene) with the required amine (A-NH$_2$) in the presence of a tertiary base (e.g. triethyl amine, or N-methylmorpholine) or an inorganic base (such as a metal bicarbonate eg sodium bicarbonate) in cold water to provide the Formula (I) compounds.

Formula (I) compounds wherein R$_1$ is 3- or 4-biphenyl are prepared by a process which comprises: reacting the corresponding Formula (I) compound wherein R$_1$ is 3-Br or 4-Br respectively with phenyl boronic acid in a suitable solvent (eg toluene-ethanol-water, 1,2-dimethoxyethane-water, tetrahydrofuran-water, or N,N-dimethylformamide-water) in the presence of a base (eg sodium carbonate, sodium bicarbonate, potassium carbonate, triethylamine) with 3 to 5 mole percent of a palladium derivative (eg palladium acetate, tetrakis(triphenylphosphine)palladium, or palladium acetate in the presence of bis(diphenylphosphino) butane) at 25 to 100° C. for 5 to 24 h.

The pyrazole-5-carboxylic acids (1) can be prepared by a process which comprises:

a) reacting a hydrazine (3), wherein R$_1$ is as defined above,

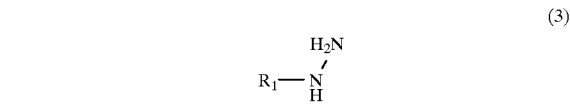

(3)

with diethyl ethoxymethylenemalonate (4)

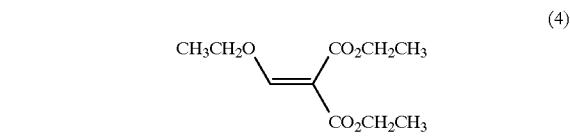

(4)

in the presence of a base such as potassium carbonate in aqueous solution to form an ester pyrazolone of Formula (5);

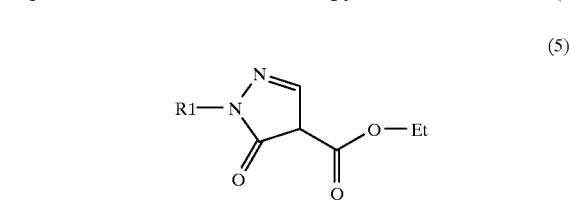

(5)

b) reacting the compound of Formula (5) above in a Mitsunobu reaction with an alcohol, R$_2$—OH (6), wherein R$_2$ is as defined above, in the presence of a tri-alkyl- or triaryl-phosphine and a dialkyl azodicarboxylate in a suitable solvent such as tetrahydrofuran, providing a compound of Formula (7);

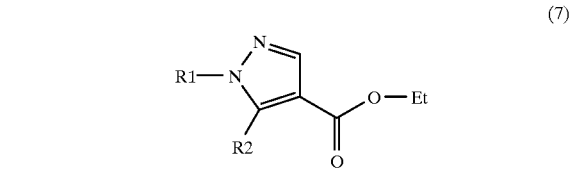

(7)

c) and saponifying the Mitsunobu reaction product above, (7), with a base such as NaOH in a mixture of ethanol and water to afford the pyrazole-5-carboxylic acid (1).

With appropriate manipulation and protection of any chemical functionality, synthesis of the remaining compounds of Formula (I) is accomplished by methods analogous to those above and to those described in the Experimental section.

In order to use a compound of the Formula (I) or a pharmaceutically acceptable salt thereof for the treatment of humans and other mammals it is normally formulated in accordance with standard pharmaceutical practice as a pharmaceutical composition.

As used herein, "modulator" means both antagonist and agonist. Preferably, the present modulators are agonists.

As used herein, "treatment" of a disease includes, but is not limited to prevention, retardation and prophylaxis of the disease.

In addition to the conditions listed hereinabove, the present compounds are useful for the treatment of diseases including but not limited to immunologically-mediated inflammatory diseases such as rheumatoid arthritis, systemic lupus erythematosus, psoriasis, eczema, multiple schlerosis, diabetes and thyroiditis. In addition, the present compounds modulate bone formation/resorption and are useful in the treatment of conditions including but not limited to ankylosing spondylitis, gout, arthritis associated with gout, osteoarthritis and osteoporosis.

Compounds of Formula (I) and their pharmaceutically acceptable salts may be administered in a standard manner for the treatment of the indicated diseases, for example orally, parentarally, sub-lingually, dermally, transdermally, rectally, via inhalation or via buccal administration.

Composition of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil. olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg/Kg, of a compound of Formula(I) or a pharmaceutically acceptable salt thereof calculated as the free base. Each dosage unit for intranasal administration contains suitably 1–400 mg and preferably 10 to 200 mg per person. A topical formulation contains suitably 0.01 to 5.0% of a compound of Formula (I).

The daily dosage regimen for oral administration is suitably about 0.01 mg/Kg to 40 mg/Kg, of a compound of Formula(I) or a pharmaceutically acceptable salt thereof calculated as the free base. The daily dosage regimen for parenteral administration is suitably about 0.001 mg/Kg to 40 mg/Kg, of a compound of Formula (I) or a pharmaceutically acceptable salt thereof calculated as the free base. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the present invention are administered in accordance with the present invention.

The biological activity of the compounds of Formula (I) are demonstrated by the following tests:

Human CB2 Cannabinoid Receptor Binding Assay

CB2 membranes are made from a polyclonal HEK 293 cell line stabily expressing the human CB2 receptor. The assay buffer comprises 50 mM Tris(pH7.4), 5 mM MgCl2, 2.5 mM EDTA and 5 mg/ml Bovine Serium Albumin Fraction V fatty acid-free(Cal Biochem). Unless otherwise noted, all chemicals are from Sigma. Tritiated 5-(1,1-dimethylheptyl)-2-(5-hydroxypropyl)cyclohexyl)-1 alpha, 2beta, 5 alpha)-phenol([$^3$H]-CP55,940,103.4 Ci/mmol, 1 mCi/ml) is purchased from DuPont NEN. Test compounds are made by Medicinal Chemistry SmithKline Beecham Pharmacuticals and are dissolved in DMSO.

The ligand binding mixture contains 1.3–1.8 nM [$^3$H]-CP55,940, 20 ug of CB2 membranes and 5 ul of each test compound in a total reaction volume of 150 ul of assay buffer. The final concentrations of compounds range from 1.00E-4 to 1.00E-10M; and the final DMSO concentration is 3.3%. The ligand binding mixtures are incubated in 96 deep well polypropylene microtiter plates for one hour at 30° C. and terminated by rapid filtration (Brandel 96-well cell harvester) over GF/B filters treated with wash buffer(50 mM Tris, 0.5 mg/ml fatty acid-free BSA, pH7.4), and followed by five washes with 3 ml ice-cold buffer. The filters are air-dried and [$^3$H]-CP55,940 bound radioactivity is determined by liquid scintillation counting. Non-specific binding is determined in the presence of 1 uM CP55,940. The binding data is analyzed with the program GraphPad Prism. $K_i$ values ranging from 1 nM to 10 uM are obtained for the compounds of the present invention.

cAMP Production In HEK293/CB2 Cells

To confirm agonist activity, the following test is conducted.

Polyclonal HEK293 cells stably expressing human CB2 receptor are maintained in EMEM media supplemented with Earl's salts, L-glutamine, 10% FBS, and 0.5 mg/ml G418 sulfate. 200 µL of cell suspension (25,000–50,000 cells/well) are added to a 96 well plate pre-treated with dilute Matrigel (Collaborative Biomedical Products: diluted 1/50 with PBS and treated for 1 hr at room temperature) and incubated at 37° C. for three days in a 5% $CO_2$ incubator.

Growth media is removed from the assay plate and each well is rinsed with 200 µL of cAMP assay buffer (EMEM media supplemented with Earl's salts, L-glutamine, 20 mM Hepes, pH 7.4, 0.1 mM $MgCl_2$ and 2 mg/ml BSA Fraction V) and blotted dry. 50 μL of assay buffer are added to each well, followed by 100 μL of 250 uM Zardaverine (a PDE 3–4 inhibitor diluted in assay buffer with 0.25% DMSO) and 50 μL of the test compound (diluted in assay buffer containing 20 mg/ml BSA and 1% DMSO). The cells are then incubated with compounds at room temperature for 30 minutes. To initiate cAMP production, 50 μL of 50 uM Forskolin (Calbiochem 344270 in assay buffer with 0.1% DMSO) is added and incubated for 15 minutes in a 37° C. incubator. The reaction is terminated by addition of 60 uL 0.2N HCl and 0.2 mM $CaCl_2$ and stored in a −80 ° C. freezer until cAMP determination.

For cAMP determinations 200 μL of cell lysate is transferred to a 96 well round-bottom plate and 40 μL of 0.1N NaOH and 0.1 mM CaCl2 is added to neutralize the lysate. Following centrifugation at 2400 rpm for 5 minutes, 20–50 μL of supernatant is assayed for cAMP using the Amersham EIA kit (RPN 225: unacetylated protocol). Using this procedure, forskolin stimulated cAMP levels range from 0.5–1.5 pmole per assay well and 5–15 pmole per original culture.

The following examples are illustrative, but not limiting of the embodiments of the present invention.

EXAMPLE 1

Preparation of N-(1-Adamantyl)-5-(2-[4-morpholinyl] ethoxy)-1-(4-isopropylphenyl)pyrazole-4-carboxamide To a stirred solution of 1-(4-isopropylphenyl)-5-(2-[4-morpholinyl]ethoxy)pyrazole-4-carboxylic acid (43 mg, 0.12 mmol) in dimethylformamide (1 mL) under an argon atmosphere, was added 1-hydroxybenzotriazole (16 mg, 0.12 mmol), 1-(3-dimethylaminopropyl)-3-ethylcarbodiimide (25 mg, 0.13 mmol), triethylamine (60 uL, 0.43 mmol) and 1-adamantanamine hydrochloride (25 mg, 0.13 mmol). The reaction mixture was stirred for 24 h at room temperature, heated to 70° C. for 2 h, and stirred for another 96 h at room temperature. The resulting mixture was treated with aqueous sodium carbonate, extracted with ethyl acetate, washed with water four times and dried over $Na_2SO_4$. The extract was concentrated in vacuo. This coupling was repeated on the same scale and the combined residue was purified by chromatography twice over silica gel eluting the first column with 2 to 3% methanol in chloroform, and the second with 30 to 40% ethyl acetate in chloroform to afford the title compound (7% yield, 8.5 mg) as a yellow powder, mp 132–134° C. MS (ES) m/e 493.4 $[M+H]^+$.

Formulations for pharmaceutical use incorporating compounds of the present invention can be prepared in various forms and with numerous excipients. Examples of such formulations are given below.

EXAMPLE 2

Inhalant Formulation

A compound of Formula (I), (1 mg to 100 mg) is aerosolized from a metered dose inhaler to deliver the desired amount of drug per use.

EXAMPLE 3

| Tablet Formulation | | |
|---|---|---|
| Tablets/Ingredients | | Per Tablet |
| 1. | Active ingredient (Cpd of Form. I) | 40 mg |
| 2. | Corn Starch | 20 mg |
| 3. | Alginic acid | 20 mg |
| 4. | Sodium Alginate | 20 mg |
| 5. | Mg stearate | 1.3 mg |

Procedure for tablet formulation:

Ingredients 1, 2, 3 and 4 are blended in a suitable mixer/blender. Sufficient water is added portion-wise to the blend with careful mixing after each addition until the mass is of a consistency to permit its conversion to wet granules. The wet mass is converted to granules by passing it through an oscillating granulator using a No. 8 mesh (2.38 mm) screen. The wet granules are then dried in an oven at 140° F. (60° C.) until dry. The dry granules are lubricated with ingredient No. 5, and the lubricated granules are compressed on a suitable tablet press.

EXAMPLE 4

Parenteral Formulation

A pharmaceutical composition for parenteral administration is prepared by dissolving an appropriate amount of a compound of formula I in polyethylene glycol with heating. This solution is then diluted with water for injections Ph Eur. (to 100 ml). The solution is then rendered sterile by filtration through a 0.22 micron membrane filter and sealed in sterile containers.

All publications, including but not limited to patents and patent applications cited in this specification are herein incorporated by reference as if each individual publication were specifically and individually indicated to be incorporated by reference as though fully set forth.

What is claimed is:

1. A compound of Formula (I):

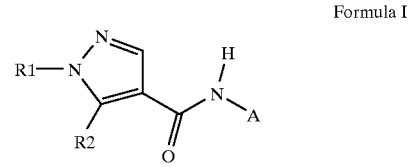

Formula I wherein:
A is selected from the group consisting of 1-adamantyl, 2-adamantyl, 3-noradamantyl, and 1,1,3,3-tetramethylbutyl;

$R_2$ is selected from the group consisting of 2-(4-morpholino)ethoxy, 2-(diallylamino)ethoxy, 2-, 3-, or 4-pyridylmethoxy, 2-(diethylamino)ethoxy, 1-methylpiperidinyl-2-methoxy, benzyloxy and 4-substituted benzyloxy;

where the substituent is selected from the group consisting of hydrogen, fluoro, chloro, methoxy, methylthio, and nitro; and $R_1$ is selected from the group consisting of $C_{1-6}$ alkyl, 3- or 4-biphenyl, unsubstituted or substituted by halo, 1-naphthyl, benzyl, phenethyl, phenyl, monosubstituted phenyl, wherein the substitutent is selected from the group consisting of hydrogen, $C_{1-4}$ alkyl, fluoro, chloro, bromo, methoxy, trifluoromethyl, and nitro, or disubstituted phenyl where the substituents are independently selected from the group consisting of fluoro, chloro, or methyl;

and pharmaceutically acceptable salts thereof.

2. A compound according to claim 1 wherein A is 1-adamantyl, 2-adamantyl or 3-noradamantyl; $R_2$ is selected from the group consisting of 2-(4-morpholino)ethoxy, 4-pyridylmethoxy, 1-methylpiperidinyl-2-methoxy, benzyloxy, and 4-fluoro-benzyloxy, and $R_1$ is phenyl, benzyl, or 4-monosubstituted phenyl wherein the substitutent is selected from the group consisting of $C_{1-4}$ alkyl, fluoro, chloro, methoxy, and trifluoromethyl.

3. A compound according to claim 2 wherein A is 1-adamantyl, $R_2$ is selected from the group consisting of 2-(4-morpholino)ethoxy, 4-pyridylmethoxy, and 1-methylpiperidinyl-2-methoxy, and $R_1$ is phenyl, benzyl, or 4-monosubstituted phenyl, wherein the substitutent is selected from the group consisting of $C_{1-4}$ alkyl, fluoro, chloro, and methoxy.

4. A compound according to claim 3 wherein $R_2$ is 2-(4-morpholino)ethoxy, and $R_1$ is phenyl-, or 4-monosubstituted phenyl wherein the substituent is $C_{1-4}$ alkyl.

5. A compound according to claim 1 selected from the group consisting of:

N-(1-Adamantyl)-1-(4-isopropylphenyl)-5-(2-(4-morpholino)ethoxy)pyrazole-4-carboxamide, N-(2-Adamantyl)-1-(4-fluorophenyl)-5-(4-pyridylmethoxy)pyrazole-4-carboxamide, N-(3-Noradamantyl)-1-(4-chlorophenyl)-5-(1-methylpiperidinyl-2-methoxy)pyrazole-4-carboxamide, N-(1-Adamantyl)-1-benzyl-5-(2-(4-morpholino)ethoxy)pyrazole-4-carboxamide, N-(2-Adamantyl)-5-(4-fluorobenzyloxy)-1-(4-methoxyphenyl)pyrazole-4-carboxamide, N-(3-Noradamantyl)-5-(benzyloxy)-1-(4-chlorophenyl)pyrazole-4-carboxamide, N-(1-Adamantyl)-1-(4-fluorophenyl)-5-(4-pyridylmethoxy)pyrazole-4-carboxamide, N-(1-Adamanty)-1-(4-chlorophenyl)-5-(1-methylpiperidinyl-2-methoxy)pyrazole-4-carboxamide, and N-(1-Adamantyl)-1-phenyl-5-(4-pyridylmethoxy)pyrazole-4-carboxamide.

6. A compound according to claim 5 which is:

N-(1-Adamantyl)-1-(4-isopropylphenyl)-5-(2-(4-morpholino)ethoxy)pyrazole-4-carboxamide.

7. A pharmaceutical composition comprising a compound according to claim 1 and a pharmaceutically acceptable carrier.

8. A method of activating cannabinoid 2 receptors which comprises administering to a subject in need thereof, an effective amount of a compound of claim 1.

9. A method of treatment of diseases exhibiting a deficiency of cannabinoid receptor 2 function, comprising administering to a subject in need thereof an effective amount of a cannabinoid receptor 2 agonist according to claim 1.

10. A method of treating an immunologically-mediated inflammatory disease selected from the group consisting of rheumatoid arthritis, psoriasis, eczema, diabetes and thyroiditis which comprises administering to a subject in need thereof an effective amount of a compound according to claim 1.

11. A method of treating a disease selected from the group consisting of ankylosing spondylitis, gout, gouty arthritis, osteoarthritis and osteoporosis which comprises administering to a subject in need thereof an effective amount of a compound according to claim 1.

12. A method of treating renal ischemia which comprises administering to a subject in need thereof an effective amount of a compound according to claim 1.

* * * * *